United States Patent [19]

Hoy

[11] Patent Number: 4,844,057
[45] Date of Patent: Jul. 4, 1989

[54] KNEE ORTHOTIC HINGE JOINT

[76] Inventor: David J. Hoy, 1095 County Rd. 2256, Perrysville, Ohio 44864

[21] Appl. No.: 121,393

[22] Filed: Nov. 16, 1987

[51] Int. Cl.⁴ ............................................. A61F 5/01
[52] U.S. Cl. ..................................... 128/80 C; 2/24; 128/88
[58] Field of Search ................. 128/80 C, 88, 80 F, 128/87 R; 2/22, 24

[56] References Cited

U.S. PATENT DOCUMENTS

| | | | |
|---|---|---|---|
| 4,463,751 | 8/1984 | Bledsoe | 128/80 C |
| 4,493,316 | 1/1985 | Reed et al. | 128/80 C |
| 4,554,913 | 11/1985 | Womack et al. | 128/80 C |
| 4,573,455 | 3/1986 | Hoy | 128/80 C |

Primary Examiner—Edgar S. Burr
Assistant Examiner—Moshe I. Cohen
Attorney, Agent, or Firm—Woodling, Krost & Rust

[57] ABSTRACT

An orthopedic hinge joint mechanism for protection of unstable or injured knees. Four coacting members are rotably fastened each to the next in a series. The first and third members lie in one plane and the second and fourth lie in an adjacent parallel plane. The members in the same plane abut in gears. As a result of this construction the hinge moves symmetrically about its center and effectivley simulates the complex action of the human knee joint.

8 Claims, 3 Drawing Sheets

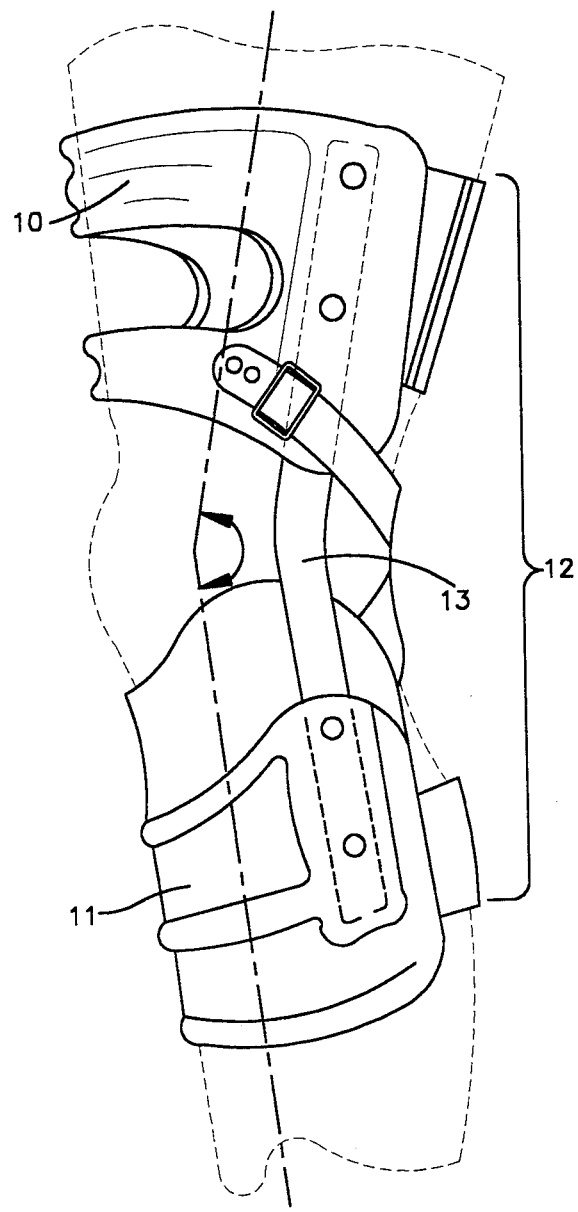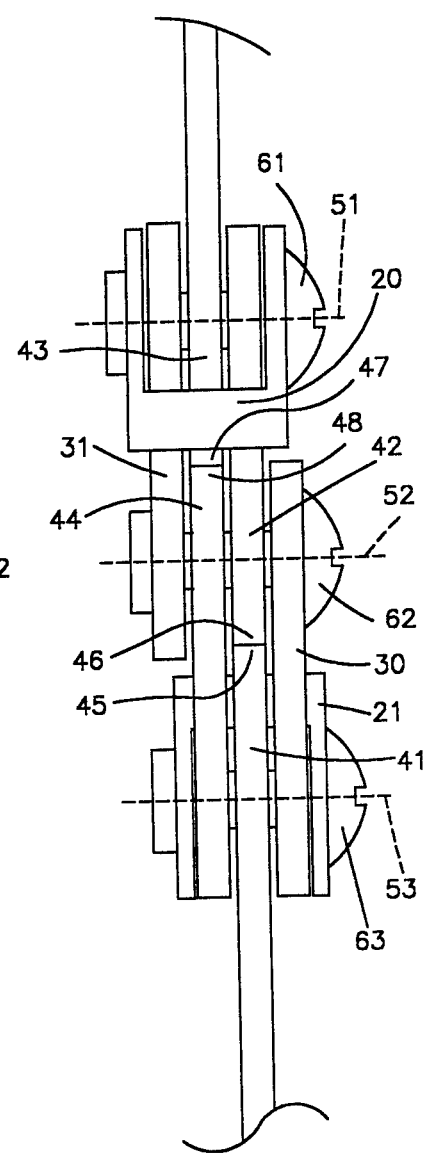
Fig.1
Fig.2

KNEE ORTHOTIC HINGE JOINT

This invention relates to orthotic devices for supporting a limited range of normal motion in limb joints. In particular, it relates to hinge joints for knee orthoses.

BACKGROUND AND SUMMARY OF THE INVENTION

Many orthotic devices have been designed to aid in the support of injured knee joints. Ideally such a device would permit the knee to move through a desired limited range of its own normal motion, but prevent it from moving into other positions which would result in further damage to the joint, such as by twisting or rotation of the leg members about their own axes, or by excessive translational movements, with respect to each other, of the leg members. The normal knee joint motion is essentially rotation about a horizontal axis passing through the knee. However, it has long been known that a simple hinge is unsatisfactory in replicating knee joint function, and a number of more complex structures, some discussed or cited in my U.S. Pat. No. 4,573,455, have been proposed.

One failing of most of the prior art devices has been that they are much too bulky to permit their use in normal activities, particularly where there is bilateral (both legs) involvement requiring two orthoses. Other problems are the failure to follow normal knee joint motion appropriately or apply adequate corrective forces, and the failure to limit extension of the lower leg to an angle required to protect the healing knee joint.

A superior prior art device has been the hinge joint mechanism of my above cited patent. This hinge joint s a polycentric multi-axial articulating series of at least four members, linked one to the other in linear series, with rotation around each axis independently. Such a structure permits any normal knee motion to be followed while it permits rotation and translation in essentially one plane only. That is, twisting of either leg member is prevented.

It has been my experience, during the use of the hinge above described, that a need exists for a similar hinge which restricts translational movement to a somewhat greater extent. In particular, the freedom of motion attained by having at least three independent axes of rotation has proven to be not always necessary. In therapeutic situations requiring a high degree of support it may, in fact, be a disadvantage.

I have now provided an improved hinge joint. Like the preferred embodiment of my previous one, it has four members linked to each other in a three-axial articulating system. However the new system is essentially different. Instead of being a linear series of members, each interior member connected only to the one before it and the one after it, and each rotating independently, the members are more intimately connected, in a non-linear fashion. Further, their rotations are restricted with respect to each other. The result is a hinge joint of great stability. Its motion is bilaterally symmetrical around a center point of the hinge, like a simple one-axis rotation, but it is not equivalent to a simple hinge. The improved joint has proven therapeutically useful in a great number of situations.

The joint is preferably covered with a flexible tubing for comfort of the wearer, to protect the hinge members from contamination by dirt and other foreign substances, and to allow sealed lubrication if desired.

It is an object of my invention to provide an improved hinge system that follows the normal knee joint motion but prevents undesired motions.

Another object of the invention is to provide such a hinge system which is compact but nevertheless exceptionally sturdy.

A further object of the invention is to provide such a hinge system the motion of which is symmetrical about its center but effectively mimics the complex motion of the human knee joint.

These objects and a fuller understanding of my invention will be more thoroughly understood from the claims appended hereunto, and from the following detailed description of a preferred embodiment in conjunction with the figures, in which FIG. 1 is a perspective view of the hinge mechanism of my invention incorporated into a typical rigid knee orthosis with tubing covering the hinge mechanisms;

FIG. 2 is a partly schematic view of the hinge mechanism itself seen from above (more properly, from the front as it is worn);

DETAILED DESCRIPTION OF A PREFERRED EMBODIMENT

FIG. 1 depicts a typical complete knee brace comprising a first or upper leg brace portion 10, a second or lower leg brace portion 11, and the hinge mechanism 12 of the subject invention firmly affixed alongside the knee to the brace portions. In FIG. 1, the hinge mechanism 12 is shown covered by tubing 13 which does not appear in the later figures. Ordinarily there will be two such hinge mechanisms, one on each side of the wearer's knee.

In FIG. 2 the central portion of the hinge mechanism 12 is seen, somewhat schematically, from above, with the front or outward face toward the right and the tubing 13 removed.

Figure 3:
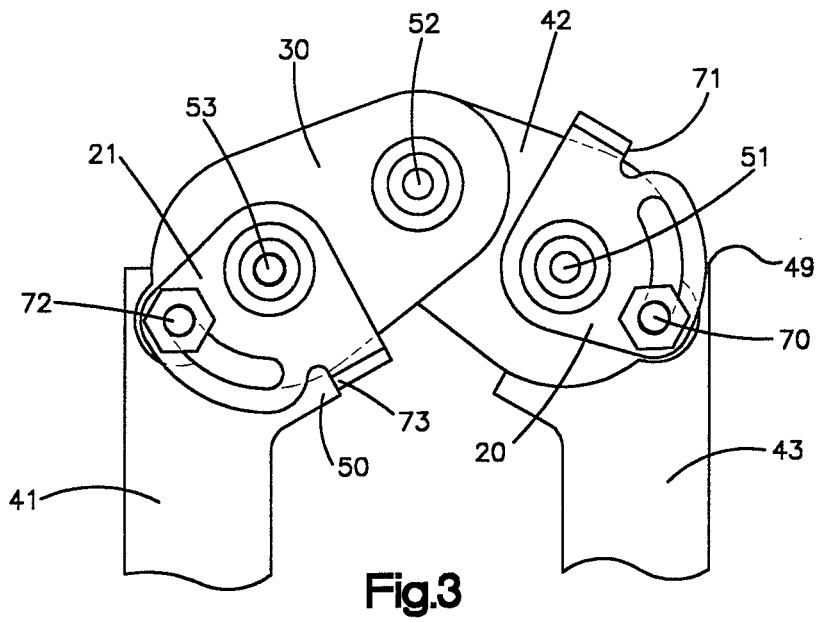
FIG. 3 is an elevational view of the hinge mechanism in its most bent position as seen from the outside (as worn)
Figure 4:
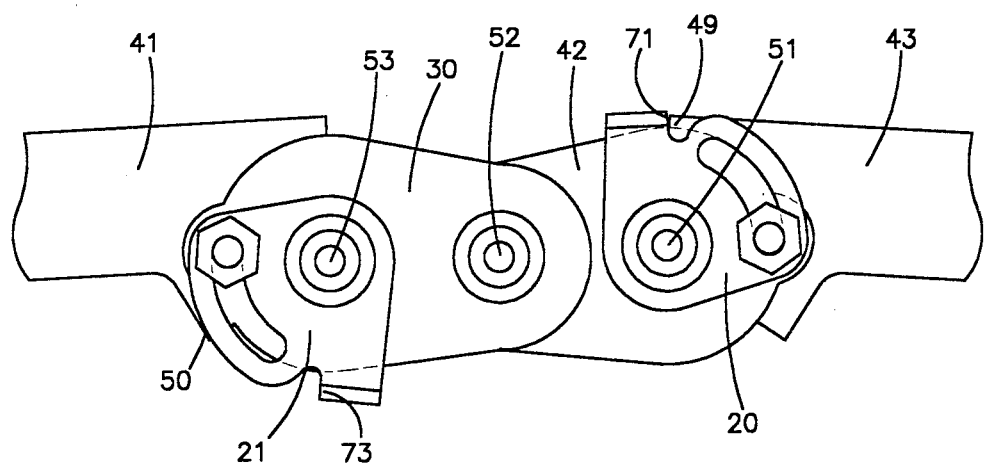
FIG. 4 is an elevational view of the hinge mechanism in its most extended position as seen from the outside.

FIGS. 3 and 4 show the hinge mechanism as seen from the front face. In FIG. 3 the hinge is bent to the maximum degree possible; in FIG. 2, and in FIG. 4 it is in the extended or substantially straight position.

FIG. 2 is the only figure showing all the members of the hinge, but FIG. 4 should be referred to also for clarity. Hinge 12 comprises an upper stop member 20 and a lower stop member 21, a front protective member 30 and a rear protective member 31, and first, second, third and fourth coacting members 41, 42, 43 and 44 respectively.

Figure 5:
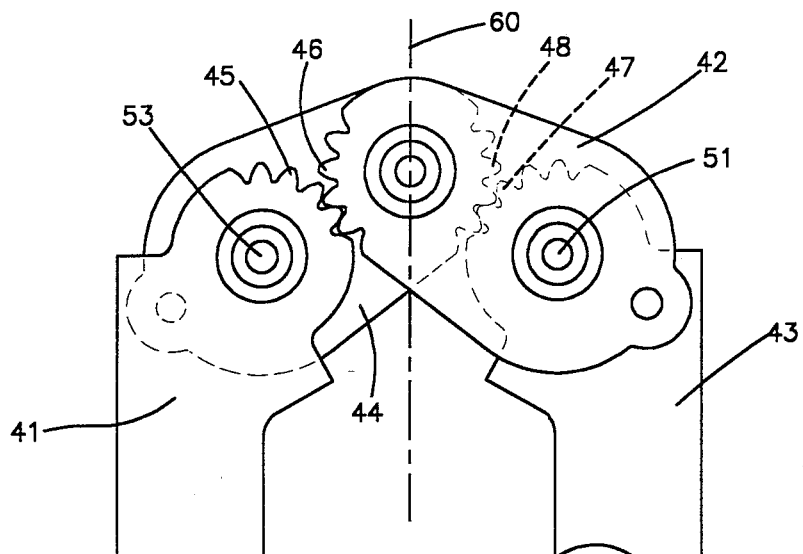
FIG. 5 is an elevational view of the innermost four members of the hinge mechanism in their most bent position.
Figure 6:
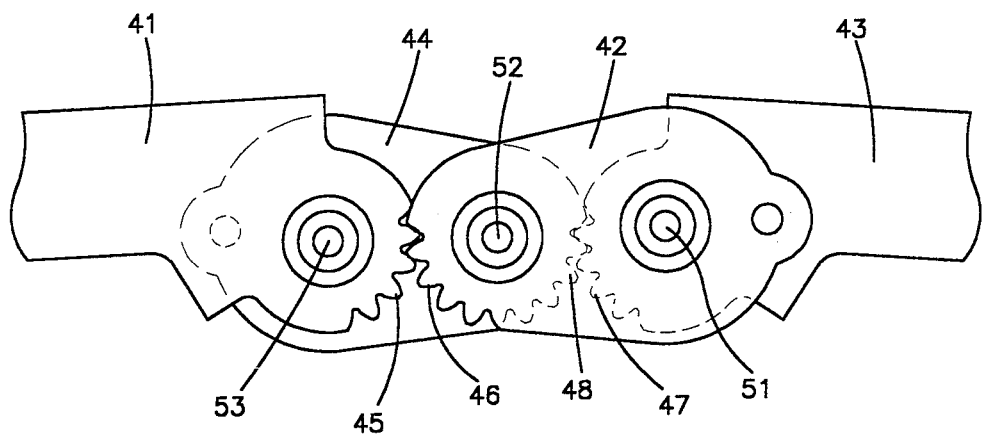
FIG. 6 is an elevational view of the innermost four members in their most extended position.

The coacting members 41 through 44 are also shown in FIGS. 5 and 6 with the other four members removed.

All members are provided with one or more holes so that rotational connections at an upper axis 51, a center axis 52 and a lower axis 53 may be made as shown by bolts 61, 62 and 63, respectively, or by any equivalent rotational hinge means.

The function of coacting members 41 through 44 will first be described as they are the most essential elements of my invention.

As best seen in FIG. 2, coacting members 41 and 42 are generally flat and occupy a rightward or front plane. They are not fastened together but abut at gear teeth 45 on member 41 and 46 on member 42. Coacting members 43 and 44 are shaped exactly like members 41 and 42, respectively, but occupy a leftward or rear plane. They also abut at gear teeth 47 and 48 (shown in phantom), respectively, in the same way. Thus, the rear (or view from the left side of the hinge) of the coacting members 41 through 44 would look exactly like FIGS. 5 and 6, except that indicia 41 and 43 would be exchanged with each other, and correspondingly 42 with 44, 45 with 47 and 46 with 48.

At axis 51, coacting members 43 and 42 are rotatably joined; at axis 52 coacting members 42 and 44, and at axis 53 coacting members 44 and 41.

Because of the exact similarity of coacting member 41 to 43 and 42 to 44, and the gear contact between the members, rotation at either of axes 51 and 53 forces a corresponding rotation at the other axis and at axis 52. That is, for any desired rotational position of coacting member 41, unique spatial relationship obtains for axes 53 and 52, which must be the same as the relationship between axes 51 and 52. Since the same holds for coacting member 43, the assemblage cannot take on any but a bilaterally symmetrical (about line 60 of FIG. 5) conformation.

It is also clear, however, by comparing FIGS. 5 and 6, that the action of the hinge is not the same as that of a single hinge joint. That action can be completely characterized by the relationships already disclosed and the distances between the axes. In practice I have found a distance of ¾ inch between axes 51 and 52 and between axes 52 and 53 to provide an excellent functional analog of the normal human knee joint.

Front protective member 30 and rear protective member 31 are exactly similar to each other and occupy a frontmost and a rearmost plane, respectively, as best seen in FIG. 2. These members 30 and 31 are functionally redundant to coacting members 44 and 42, respectively, being mounted on the same axes, but they are preferred as they help assure that the gears are protected on both sides.

Upper stop member 20 and lower stop member 21 are mounted on axes 51 and 53, respectively. Upper stop member 20, as best seen in FIG. 3 and 4, is rotably affixed to second coacting member 42 at axis 51 but is provided with upper screw means 70 so that its rotational orientation with respect to second coacting member 42 may be held at any of a range of desired angles. A shoulder 71, extending from the front to the rear, abuts a shoulder 49 on coacting member 43 to limit the range of extension or straightening of the joint. As depicted, extension to a maximum is permitted, but it will readily be seen that a readjustment of upper stop member 20 at upper screw means 70 will rotate upper stop member 20 clockwise and cause abutment of shoulders 71 and 49 at a position of less extension as desired. In exactly similar fashion, lower stop member 21 has lower screw means 72, and shoulder 73 which abuts a shoulder 50 on first coacting member 41 when the hinge is closed to the angle desired to be the minimum. This is an important feature in protecting the healing knee joint.

Only the central portion of my hinge has been shown in FIGS. 2 through 6, it being understood that coacting members 41 and 43 are provided with extensions permitting their being affixed to a typical brace such as that shown in FIG. 1.

Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and the scope of the invention as hereinafter claimed.

I claim:

1. A hinge mechanism for following the motion of the human knee, said hinge mechanism comprising
    a first member;
    a second member rotably connected to said first member at a first axis of rotation;
    a third member rotably connected to said second member at a second axis of rotation distinct from said first axis; and
    a fourth member rotably connected to said third member at a third axis of rotation distinct from said first and second axes;
    said first and third members being in toothed rolling abutment and said second and fourth members being in toothed rolling abutment.

2. The hinge mechanism of claim 1 and further comprising stop means restricting the rotational angle between said first and fourth members to lie above a desired angle.

3. The hinge mechanism of claim 1 and further comprising stop means restricting the rotational angle between first and fourth members to lie below a desired angle.

4. The hinge mechanism of claim 1 and further comprising a length of flexible tubing extending over and encasing the rotable connections of said hinge mechanism in the regions of said rotable connections.

5. The hinge mechanism of claim 1 and further comprising
    a fifth member covering said toothed rolling abutment of said first and third members and
    a sixth member covering said toothed rolling abutment of said second and fourth members.

6. The hinge mechanism of claim 5 and in which said toothed rolling abutment of said first and third members occurs in a first plane and said toothed rolling abutment of said second and fourth members occurs in a second plane parallel to said first plane.

7. The hinge mechanism of claim 1 and in which said toothed rolling abutment of said first and third members occurs in a first plane and said toothed rolling abutment of said second and fourth members occurs in a second plane parallel to said first plane.

8. The hinge mechanism of claim 7 and further comprising a length of flexible tubing extending over and encasing the rotable connections of said hinge mechanism in the regions of said rotable connections.

* * * * *